United States Patent [19]

Matsumoto et al.

[11] Patent Number: 5,043,156
[45] Date of Patent: Aug. 27, 1991

[54] METHOD OF TREATING INFECTIOUS DISEASES WITH GRANULOCYTE COLONY-STIMULATING FACTOR

[75] Inventors: Masahiko Matsumoto; Shuzo Matsubara, both of Shizuoka, Japan

[73] Assignee: Chugai Seiyaku Kabushiki Kaisha, Tokyo, Japan

[21] Appl. No.: 275,343

[22] Filed: Nov. 23, 1988

Related U.S. Application Data

[63] Continuation of Ser. No. 109,082, Oct. 16, 1987, abandoned.

[30] Foreign Application Priority Data

Oct. 18, 1986 [JP] Japan .......................... 61-248048

[51] Int. Cl.$^5$ .......................................... A61K 37/02
[52] U.S. Cl. .................................... 424/85.1; 514/2; 514/8; 514/21; 530/350; 530/351; 530/395; 530/820; 530/808; 435/69.5; 435/70.1
[58] Field of Search ............... 530/350, 351, 395, 820, 530/808; 435/69.5, 70.1; 424/85.1; 514/2, 8, 21

[56] References Cited

U.S. PATENT DOCUMENTS

| | | | |
|---|---|---|---|
| 4,621,050 | 11/1986 | Sugitomo | 435/68 |
| 4,808,611 | 2/1989 | Cosman | 514/12 |
| 4,810,643 | 3/1989 | Souza | 435/68 |
| 4,833,127 | 5/1989 | Ono | 514/21 |

FOREIGN PATENT DOCUMENTS

118915 9/1984 European Pat. Off. .
86/00639 1/1986 World Int. Prop. O. .

OTHER PUBLICATIONS

Durack, D. T. Infection in Compromised Hosts In: *Clinical Aspects of Immunology* Ed. Lachmann, P. J. and Peters, D. K. (1982) pp. 1713–1751.
Henderson, E. S. The Granulocytopenic Effects of Cancer Chemotherapeutic Effects. In: *Drug and Hematologic Reactions.* (1974), pp. 207–221.
Rodriguez, V. and Bodey, G. P. (1976), Clin. Hematol. 5: 347–360.
Dale, D. C. et al., (1974) J. Clin. Invest. 54: 664–671.
McCredie, K. B. and Hester, J. P. (1976) Clin. Hematol. 5: 379–394.
Motoyoshi, K. et al., (1982) Jap. J. Med. 21: 187–191.
Kohski, M. et al., (1983) Proc. Natl. Acad. Sci. 80: 3802–3806.
Lee, M. and Hopkins, L. E. (1980) Amer. J. Hosp. Pharm. 37: 1066–1071.
Bodey, G. P. et al. (1966) Ann. Int. Med. 64: 328–340.
Sleijfer, D. T. et al. (1980) Europ. J. Cancer 16: 859–869.
Cass, C. E. et al. (1981) Cancer Res. 41: 1000–1005.
Klastersky, J. et al., (1973) Cancer 31: 331–336.
Shibata, H. (1986) Clinical Assay 30: 1105–1111.
Tsuneoka, K. and Shikita, M. (1984) Cell Struct. Funct.

Neumeier, R. and Maurer, H. R. (1981) In: *Electrophoresis '81* Ed. R. C. Allen and P. Armaud. pp. 729–734.
Nomura, H. et al., (1986) EMBO 5: 871–876.
Burgess, A. W. et al., Blood (1977) 49: 573–583.
Stanley E. R. et al. J. Biol. Chem. (1977) 252: 4305–4312.
Burgess, A. W. et al., J. Biol. Chem. (1977) 252: 1998–2003.
Dipersio, J. F. et al., Blood (1978) 51: 507–519.
Wu, M. C. et al., J. Biol. Chem (1979) 254: 6226–6228.
Nicola, N. A. et al., Blood (1979) 54: 614–654.
Burgess, A. W. et al., In J. Cancer (1980) 26: 647–654.
Dipersio et al., Blood, Journ. of the Am. Soc. of Hematol (1980) 56: 717–727.
Okabe, T. et al., J. Cell. Physiol. (1982) 110: 43–49
Okabe, T. et al., J.N.C. 1 (1982) 69(6) 1235–1243.
Schlunk, T. et al., Blut (1983) 47: 211–223.
Nicola, N. A. et al., J. Biol. Chem. (1983) 258: 9107–9023.
Clark-Lewis, I. et al., J. Biol. Chem. (1984) 259: 7488–7494.
Gasson, J. C. et al., Science (1984) 226: 1339–1342.
Welte, K. et al., J. Cell. Biochem. (1985) Supp 9A 116.
Jubinsky, P. T. et al., Proc. Natl. Acad. Sci. USA (1985) 82: 2764–2768.
Nicola N. A. et al., Nature (1985) 314: 625–628.
Welte, K. et al., Proc. Natl. Acad. Sci. U.S.A. (1985) 82. 1526–1530.
Fojo, S. S. et al., Biochemistry (1978) 17: 3109–3116.
Motoyoshi, K. et al., Blood (1978) 52: 1012–1020.
Waheed, A. et al. J. Lab. Clin. Med. (1979) 94: 180–194.
Waheed, A. et al. Blood (1982) 60: 238–244.
Neumeier, R. et al. Hoppe-Seyler's Z. Physiol. Chem. (1982) 363: 1493–1500.
Wang, F. F. et al. J. Cell. Biochem. (1983) 21: 263–275.
Fujisawa, M. et al. (Sep. 1986) Jpn. J. Cancer Res. 77: 866–869.
Zsebo, K. et al. (1986) Immunobiol. 172: 175–184.
Tomida, M. et al. (Oct. 1986) FEBS 207: 271–275.
Messner, M. A. et al. Blood (1973) 42: 701.
Golde, D. V. et al. Blood (1978) 52: 1068–1072.

(List continued on next page.)

*Primary Examiner*—Garnette D. Draper
*Attorney, Agent, or Firm*—Morgan & Finnegan

[57] ABSTRACT

A method of treating an infectious disease by administering both a granulocyte colony stimulating factor (G-CSF) and an antimicrobial agent is disclosed. Also disclosed is a kit for treatment of an infectious disease that comprises an antimicrobial agent and a pharmaceutical drug having G-CSF as the effective ingredient. The resistance of a patient against infection is enhanced by administration of G-CSF, and this augments the therapeutic effect of an antimicrobial agent to be subsequently administered. By the synergistic effect of G-CSF and the antimicrobial agent, the infectious diseases can be treated in a very effective manner.

8 Claims, No Drawings

OTHER PUBLICATIONS

Okabe, I. et al. Cancer Res. (1978) 38: 3910-3917.
Stanley, E. R. et al. Proc. Natl. Acad. Sci. USA (1979) 76: 2969-2973.
Wu, M. C. et al. J. Clin. Invest. (1980) 65: 772-775.
Lusis et al. Blood, Journ of the Am. Soc. of Hematol. (1981) 57: 13-21.
Nicola, N. A. et al. J. Cell. Physiol. (1981) 112: 257-264.
Metcalf, D. et al., Natl. Cancer Inst. Monogr., (1982), 60: 123-131.
Metcalf, D. et al., Int. J. Cancer, (1982), 30: 203-210.
Metcalf, D. et al., Int. J. Cancer, (1982), 30: 773-780.
Vadas, M. A. et al., J. Immunol., (1983), 130: 795-799.
Ihle, J. N. et al., J. Immunol., (1983), 131: 282-287.
Lopez, A. F. et al., J. Immunol., (1983), 131: 2983-2988.
Begley, C. G. et al., Exp. Hematol, (1985), 13: 956-962.
Gabrilove et al., Proc. Natl. Acad. Sci. USA, (1986), 83: 2478-2482.
Weinstein et al., Proc. Natl. Acad. Sci. USA, (1986), 83: 5010-5014.
Metcalf, D. et al., Leuk. Res., (1983), 7: 117-132.
Metcalf, D. et al., Leuk. Res., (1985), 9: 35-50.
Abboud, C. N. et al., Blood, (1981), 58: 1148.
Vadas, M. A. et al., J. Immunol., (1984), 133: 202.
Shah, R. G. et al., Blood, (1977), 50: 811-821.
Neumeier, R. et al., Blut, (1982), 44: 21-27.
Yung, Y. P. et al., J. Immunol., (1982), 129: 1256-1261.
Metcalf, D. et al., J. Cell. Physiol., (1983), 116: 198-206.
Wang, F. F. et al., J. Cell. Biochem., (1983), 21: 263-175.
Nagata, S., et al., (Mar. 1986), EMBO, 5: 575-581.
Nagata, S., et al., (Jan. 1986), Nature, 319: 415-418.
Souza, L., et al., (Apr. 1986), Science, 232: 61-65.
Tsuchiya, M., et al., (Oct. 1986), Proc. Natl. Acad. Sci., 83: 7633-7637.
Gough, N. M. et al., Nature, (1984), 309: 763-767.
Wong, G. G. et al., Science, (1985), 228: 810-815.
Lee, F. et al., Proc. Natl. Acad. Sci. USA, (1985), 82: 4360.
Bradley, T. R., et al., (1966), Aust. J. Exp. Med. Sci., 44: 287-300.
Das, S. K., et al., (1980), J. Cell Physiol., 104: 359-366.
Metcalf, D., et al., (1977), Hemopoietic Colonies: In Vivo Cloning of Normal and Leukemic Cells. Springer, Berlin.
Nicola, N. A., et al., (1985), Methods Enzymol., 116: 600-619.

METHOD OF TREATING INFECTIOUS DISEASES WITH GRANULOCYTE COLONY-STIMULATING FACTOR

This is a continuation of copending application Ser. No. 109,082, filed Oct. 16, 1987, now abandoned.

BACKGROUND OF THE INVENTION

The present invention relates to an effective method against infectious diseases by chemotherapy involving the use of a granulocyte colony stimulating factor (hereinafter abbreviated as G-GSF) in combination with antimi crobial chematherapy.

The progress and termination of infections are generally determined by the interrelation between the host resistance to infection, the virulence of an infectious microorganism and the antimicrobial activity of the chemotherapeutic agent used.

Recent advances in chemotherapeutics have been so remarkable as to enable the development of broad-spectrum and potent antimicrobial agents that are effective not only against common pathogenic bacteria but also against "opportunistic" bacteria which cause disease only in an immunocompromised host. The life-span of individuals has increased in recent years, because the incidence of death caused by infection has been reduced by administration of broad-spectrum and potent antimicrobial agents.

However, even the best antimicrobial agents available today are incapable of exhibiting high efficacy in patients whose immunologically competent cells such as neutrophils, macrophages and lymphocytes are either damaged or insufficiently produced. For instance, administration of anticancer agents, X-irradiation, or administration of immunosuppressants damages hematopoietic organs in the patient and causes a reduction of the number of immunocompetent cells or impairment of their functions. Patients in this state, who are called risk patients, usually suffer recurrent infections which are very serious in severity and often result in fatality. Therefore, it cannot be overemphasized how critical it is that the success of patient care during cancer treatment or organ transplantation depends entirely upon how the patient is protected from infection.

Causative microorganisms that are frequently detected in risk patients suffering from infections include bacteria such as *Staphylococcus aureus, Staphylococcus epidermidis, Streptococcus pyogenes, Streptococcus pneumoniae, Enterococcus faecalis, Hemophilus influenzae, Escherichia coli, Klebsiella pneumoniae, Enterobacter cloacae, Citrobacter freundii, Serratia marcescens, Pseudomonas aeruginosa* and *Pseudomonas maltophilia*, and fungi such as *Candida albicans* and *Aspergillus fumigatus*. In clinical antimicrobial agents such as those based on penicillin, cephalosporin and aminoglycosides are administered according to the site of occurrence and the severity of disease. In addition, antipyretics, analgesics, antiinflammatories and other appropriate agents are administered as nosotropic drugs.

As mentioned above, broad-spectrum and potent antimicrobial agents have been developed in recent years but their therapeutic effects are not exhibited enough if the patient's immunity is lowered. There have been many clinical cases reported in which the bacteria and fungi listed above cause infection in patients whose neutrophils are abnormally small in number or fail to exhibit their function in a normal way. Actually, mice to which anticancer agents such as cyclophosphamide, neocarzinostatin, mitomycin and 5-FU have been administered become highly susceptible to the microorganisms. The infected mice will be killed eventually.

In response to the infecting bacteria, neutrophils rapidly migrate to the infection site and phagocytize or kill bacteria to eliminate them. In this respect, neutrophils are very important effector cells that protect against the expansion of bacteria in the body.

In general, peripheral blood neutrophils in normal volunteers are 1800–6700/mm$^3$. When peripheral blood neutrophils decrease to 500–1000/mm$^3$ or less, not only does the incidence of infection increase but also chemotherapeutic effect is difficult to obtain even if patients are applied any antibiotics. A certain way to augment the number and function of matured neutrophils is strongly requested by clinicians. If it would be supplied by a new drug, the cure rate in infections could be improved and the total dose of an antimicrobial agent reduced, accompanied by a corresponding decrease in the occurrence of side effects due to the administration of the antimicrobial agent. As a further advantage, it would be possible for the therapeutic effect of a certain antimicrobial agent to materialize even against an infectious disease that is inherently difficult to cure with such agent.

SUMMARY OF THE INVENTION

The present invention provides a drug that enhances the effectiveness of chemotherapy for a risk patient whose neutrophiles have reduced in number or deteriorated in function.

The present invention also provides a method for treating infectious diseases by the agency of such a drug.

Furthermore, the present inventors conducted intensive studies with a view to solving the aforementioned problems encountered in the treatment of infectious diseases that have attacked immunocompromised hosts with underlying diseases. As a result, the present inventors found that by combined administration of G-CSF and antimicrobial agents, the host resistance will be activated while the pharmacological effect of the administered antimicrobial agent will be enhanced, thereby ensuring effective treatment of an infectious disease. The present invention has been accomplished on the basis of this finding.

The method of the present invention is characterized in that G-CSF is administered to a patient who is or will be suffering from leukopenia or a patient who has been infected with a certain disease and they are then treated with an antimicrobial agent.

DETAILED EXPLANATION OF THE INVENTION:

The G-CSF used in the present invention may be derived from any source of origin so long as the source is capable of producing a human G-CSF of high purity. A desired human G-CSF can be produced by any of the following methods: it may be extracted, separated and purified from a human viable sample; human G-CSF producing cells may be cultivated and a desired human G-CSF isolated from the supernatant of the culture; a desired human G-CSF may be obtained from a human G-CSF producing hybridoma that has been prepared by cell fusion techniques; a host such as *E. coli* or animal cells may be transformed by gene recombinant technology and the human G-CSF, produced from the transformant, isolated and purified; or alternatively, any of the G-CSF samples prepared by the above procedures may be chemically modified. A polypeptide that is produced as a result of polymorphism occurring in the process of transformation, as known in the case of a human interferon gene (Ohno et al., Proc. Nat. Acad. Sci., USA, 77, 5305, 1981), which lacks one or more amino acids in the amino acid sequence to be described below, or which has one or more amino acids replaced by one or more other amino acids, may be employed if it has a human G-CSF activity.

Two particularly preferred examples of human G-CSF are the following (1) and (2), which have already been successfully prepared by the present inventors and are available in large quantities in a highly pure and homogeneous form:

(1) human G-CSF having the following physicochemical properties:
  i) molecular weight: about 19,000 ±1,000 as measured by electrophoresis through a sodium dodecylsulfate-polyacrylamide gel;
  ii) isoelectric point: having at least one of the three isoelectric points, $pI = 5.5 \pm 0.1$, $pI = 5.8 \pm 0.1$, and $pI = 6.1 \pm 0.1$;
  iii) ultraviolet absorption: having a maximum absorption at 280 nm and a minimum absorption at 250 nm;
  iv) amino acid sequence of the 21 residues from N terminus:

H₂N—Thr—Pro—Leu—Gly—Pro—Ala—Ser—Ser—Leu—Pro—
Gln—Ser—Phe—Leu—Leu—Lys—Cys—Leu—Glu—Gln—Val—

(2) human G-CSF containing either a polypeptide having the human granulocyte stimulating factor activity which is represented by all or part of the amino acid sequence shown below, or a glycoprotein having both said polypeptide and a sugar chain portion:

$(Met)_n$Thr—Pro—Leu—Gly—Pro—Ala—Ser—Ser—Leu—Pro
Gln—Ser—Phe—Leu—Leu—Lys—Cys—Leu—Glu—Gln—Val
Arg—Lys—Ile—Gln—Gly—Asp—Gly—Ala—Ala—Leu—Gln
Glu—Lys—Leu—(Val—Ser—Glu)$_m$Cys—Ala—Thr—Tyr—Lys
Leu—Cys—His—Pro—Glu—Glu—Leu—Val—Leu—Leu—Gly
His—Ser—Leu—Gly—Ile—Pro—Trp—Ala—Pro—Leu—Ser
Ser—Cys—Pro—Ser—Gln—Ala—Leu—Gln—Leu—Ala—Gly
Cys—Leu—Ser—Gln—Leu—His—Ser—Gly—Leu—Phe—Leu
Tyr—Gln—Gly—Leu—Leu—Gln—Ala—Leu—Glu—Gly—Ile
Ser—Pro—Glu—Leu—Gly—Pro—Thr—Leu—Asp—Thr—Leu
Gln—Leu—Asp—Val—Ala—Asp—Phe—Ala—Thr—Thr—Ile
Trp—Gln—Gln—Met—Glu—Glu—Leu—Gly—Met—Ala—Pro
Ala—Leu—Gln—Pro—Thr—Gln—Gly—Ala—Met—Pro—Ala
Phe—Ala—Ser—Ala—Phe—Gln—Arg—Arg—Ala—Gly—Gly
Val—Leu—Val—Ala—Ser—His—Leu—Gln—Ser—Phe—Leu
Glu—Val—Ser—Tyr—Arg—Val—Leu—Arg—His—Leu—Ala
Gln—Pro (provided that m is 0 or 1; and n is 0 or 1).

The human G-CSFs (1) and (2) may be produced by the methods described in the Referential Examples shown later in this specification. Stated more specifically, human G-CSF (1) can be prepared by the method described in Referential Example 1, human G-CSF (2) by the method described in Referential Example 2.

For details of the conditions employed for performing these methods, see the specification of Japanese Patent Application Nos. 53273/1984, 269455/1985, 269456/1985, 270838/1985 and 270839/1985, all having been filed by the assignee of the present invention.

Another method that can be employed consists of performing fusion of a G-CSF producing cell with a selfproliferating malignant tumor cell and cultivating the resulting hybridoma in the presence or absence of mytogen.

All of the human G-CSFs that are prepared by the methods described above are included within the scope of the present invention.

The method of the present invention for treatment of infectious diseases has been accomplished on the basis of the finding already described. The antimicrobial agent that can be used in this method is by in no way limited and may be selected from among those which are currently employed to treat infectious diseases caused by various organisms. Examples of antimicrobial agents useful in the treatment of Pseudomonas aeruginosa caused infection include: β-lactam based drugs such as Carbenicillin (CBPC from Fujisawa Pharmaceutical Co., Ltd.), Sulbenicillin (SBPC from Takeda Chem. Ind. Co., Ltd.), Piperacillin (PIPC from Toyama Chemical Co., Ltd.), Ceftazidine (CAZ from Glaxo Lbs., Ltd.), Cefsulodin (CSF from Takeda Chem. Ind. Co., Ltd.) and Cefoperazone (CPZ from Toyama Chemical Co., Ltd.); aminoglycosides such as Gentamicin (GM from Schering-Plough Corp.), Amikacin (AMK from Bristol-Myers Co.) and Dibekacin (DBK from Meiji Seika Co., Ltd.); and quinolone carboxylic acid based drugs such as Norfloxaoin (NFLX from Kyorin Pharmaceutical Co., Ltd.) and Ofloxacin (OFLX from Daiichi Seiyaku Co., Ltd.)

The method of the present invention which consists of administering both G-CSF and antimicrobial agents is applicable to any infectious diseases that are caused by organisms such that neutrophils are considered to play a relatively important role in their elimination from the body, and among these organisms are *Streptococcus pyogenes, Streptococcus pneumoniae, Staphylococcus epiderdis, Enterococcus faecalis, Hemophilus influenzae, Escherichia coli, Klebsiella pneumoniae, Enterobacter cloacae, Serratia marcescens, Pseudomonas aeruginosa, Pseudomonas maltophilia, Candida albicans, Aspergillus fumigatus*, and combinations of these species.

In the treatment of infectious diseases by the method of the present invention, G-CSF may be administered to a patient who is or will be suffering from leukopenia or to a patient who has been infected with a certain disease. Any known route can be utilized in administering the G-CSF and it may be formulated in a suitable dosage form according to the specific route of administration selected. Since G-CSF is typically obtained as a G-CSF containing solution by any of the methods described above, it may be stored in a frozen state after being further purified and concentrated, as required, by any known techniques. Alternatively, the solution may be stored after being dehydrated by such means as freeze-drying or vacuum drying. If desired, the human G-CSF may be dissolved in an appropriate buffer, followed by aseptic filtration through a Millipore filter or any other suitable means so as to formulate in injection.

In order to formulate a dosage form that is suitable for administration to the patient through a certain route, the G-CSF to be used in the method of treatment of the present invention may contain an appropriate additive selected from among known pharmaceutical carriers, excipients, diluents, stabilizers and anti-adsorption agents. The additives that can be used are known and are in no way limited to particular examples.

The level of dosage and the frequency of administration of the G-CSF may be appropriately determined in consideration of various factors such as the severity of the infectious disease to be treated, the type of the causative organisms, the body weight, age and sex of the patient, and the route of administration. Typically, a dosage containing 0.1–500 μg, preferably 0.5–200 μg, of G-CSF may be administered to an adult one to several times a week.

In normal mice, rats and monkeys, G-CSF did not cause any adverse effects: G-CSF was administered to mice for 21 consecutive days in a dose of 2.5 μg on a once-a-day basis; it was administered for 16 consecutive days in a dose of 5 μg on a twice-a-day basis; and it was administered to monkeys for 14 consecutive days in a dose of 20 μg on a once-a-day basis, and, alternatively, once in a dose of 50 μg. These doses were about 30 times the effective dose. Therefore, dose levels used are considered to be completely safe. It is to be noted that the present invention is in no way limited by the dose of G-CSF employed and it may be administered in doses higher than the above-noted levels.

In the method of the present invention, a variety of known antimicrobial agents may be used depending upon the causative microorganism of the infectious disease to be treated. In general, two or more antimicrobial agents are applied in combination with respective safe effective doses.

The order in which G-CSF and an antimicrobial agent are administered is in no way limited but, in general cases, a patient who is or will be suffering from leukopenia or a patient who has been infected with a certain disease is first given G-CSF, and antimicrobial agents are then administered.

The assignee of the present invention previously demonstrated that G-CSF had the ability to protect hosts from various causative microorganisms of infection (see Unexamined Published Japanese Patent Application No. 186327/1986 or WO 86/04506). Since G-CSF itself has no ability to kill microorganisms, the protecting effect of G-CSF is believed to be exhibited as a result of it activating the host resistance against infections. Treatment of infectious diseases is usually carried out using antimicrobial agents but since G-CSF has experimentally been found to enhance the resistance of hosts to infection, it is suggested that the use of both G-CSF and an antimicrobial agent has a synergistic effect in increasing the therapeutic effect of the antimicrobial agent. In order to verify this possibility therapeutic experiments were conducted on "risk" patients who had been infected with the following organisms: *Pseudomonas aeruginosa, Escherichia coli, Klebsiella pneumoniae, Serratia marcescens, Staphylococcus aureus, Streptococcus pyogenes,* and *Candida albicans.* Even in neutropenic mice that were infected to such an extent that there was hardly any possibility of them being cured with known antimicrobial agents, the combined administration of G-CSF and an antimicrobia agent exhibited a very high therapeutic effect. This result suggests that the combined use of G-CSF and an antimicrobial agent will be effective in curing diseases that have been considered refractory and that this will eventually lead to a reduction in the amount of antimicrobial agent used. It is also anticipated that the reduced use of antimicrobial agents will contribute to a dramatic decrease in the sort of side effects that have hitherto been considered to be serious problems in the practice of chemotherapy.

EXAMPLES

The following example and referential examples are provided for the purpose of further illustrating the present invention and for demonstrating the therapeutic effect thereof.

REFERENTIAL EXAMPLE 1

Preparation of Human G-CSF by Cultivation of G-CSF Producing Cells

A G-CSF producing cell strain CHU-1 (C.N.C.M. Accession Number I-315), derived from the tumor of a patient with oral cavity cancer and established by the method described in Example 1 given in the specification of Japanese Patent Application No. 153273/1984, or a cell strain CHU-2 (C.N.C.M. Accession Number I-483) that had been established by a similar method, was suspended in an RPMI 1640 culture solution containing a bovine fetal serum, transferred into a glass roller bottle, and whirl-cultured. When the cells became confluent on the inner wall of the roller bottle, the culture solution was replaced by a serum-free RPMI 1640. After a 4-day cultivation period, the supernatant of the culture was recovered and cultivation was continued with a serum-free RPI 1640 being added. After a 3-day cultivation period, the culture solution was again replaced by a serumfree RPMI 1640 and the supernatant of the culture was recovered 4 days later. By repeating these procedures, a serum-free supernatant of the culture was obtained. This supernatant was concentrated by about 1,000 fold by ultrafiltration, purified and subsequently assayed.

The procedures of purification and assay were the same as those described in the examples given in the specification of Japanese Patent Application No. 153273/1984.

REFERENTIAL EXAMPLE 2

Preparation of Human G-CSF by Gene Recombinant Technology

A cDNA fragment harboring the human G-CSF gene was cut from *E. coli* strain X1776R-2 that had been deposited by the assignee of the present invention with the Fermentation Research Institute, the Agency of Industrial Science and Technology, under deposit number FERM BP-955. This fragment was incorporated into a vector pdKCR to construct plasmid pHGV2. The plasmid was treated with SalI and subjected to reaction with aDNA polymerase-Klenow fragment.

An EcoRI linker was attached to the resulting DNA, which was again digested partially with EcoRI. A fragment of about 2.7 kb was recovered by electrophoresis through an agarose gel.

In a separate step, plasmid pAdD26SVpA [Kaufman, R. G. & Sharp, P. A. (1982) Mol. Cell Biol., vol. 2, 1304–1319] was treated with EcoRI and subsequently dephosphorylated by treatment with BAP. Following a treatment with phenol, the EcoRI fragment of pAdD26SVpA was recovered by electrophoresis.

This pAdD26SVpA fragment was annealed with the previously obtained 2.7 kb fragment and the so obtained DNA was used to transform *E. coli* strain DHI using the rubidium chloride procedure, so as to obtain plasmid pHGV2-dhfr.

CHO cells (dhfr⁻ strain; courtesy of Dr. L. Chasin of Columbia University) were cultivated for growth in an alphaminimal essential medium containing 10% calf serum (α-MEN supplemented with adenosine, deoxyadenosine and thymidine) in plates 9 cm⌀, Nunc). The cultured cells were transformed by the calcium phosphate procedure [Wigler et al., cell, 14, 725 (1978)] in the following manner.

A carrier DNA (calf thymus DNA) was added in an appropriate private amount to 1 μg of the plasmid pHGV2-dhfr prepared above, and the mixture was dissolved in 375 μl of a TE solution, followed by addition of 125 μl of 1 M $CaCl_2$. After the solution was cooled on ice for 3-5 minutes, 500 μl of 2 ×HBS (50 mM Hepes, 280 mM NaCl, and 1.5 mM phosphate buffer) was added to the solution. After re-cooling on ice, the solution was mixed with 1 ml of the culture of CHO cells, transferred onto plates, and incubated for 9 hours in a $CO_2$ incubator. The medium was removed from the plate and, following washing with TBS (Tris-buffered saline), addition of 20% glycerol-containing TBS, and re-washing, a non-selective medium (the α-MEN medium described above except that it was supplemented with nucleotides) was added. After a 2-day incubation, a 10-fold dilution of the culture was transferred onto a selective medium (not supplemented with nucleotides). The cultivation was continued, with the medium being replaced by a fresh selective medium every 2 days, and the resulting foci were selected and transferred onto fresh plates, where the cells grew in the presence of 0.02 μM methotrexate (MTX), followed by cloning through growth in the presence of 0.1 μM MTX.

The cloning was further continued and as a result, at least 0 mg/L of human G-CSF was found to have been produced.

The procedures of purification and assay of the human G-CSF were identical to those described in Examples 2 and 5 given in the specification of Japanese Patent Application No. 269456/1985.

The microorganisms, antimicrobial agents, animals and method employed in Referential Examples 3-5 and the Example were as follows.
Microorganism: See Table 1.
Antimicrobial agent: See Table 1.
Animal: 7-9 week old male CD-1 (ICR) mice (Japan Charles River Co.)
Method: Cyclophosphamide (CPA; Endoxan from Shionogi & Co., Ltd.) which is known as an anti-cancer agent was administered intraperitoneally to the ICR mice in a dose of 200 mg/kg so as to cause neutropenia. Four days later, the treated mice and untreated normal mice (control) were infected. Starting on the day after CPA, G-CSF was administered 4 times on a once-a-day basis. An antimicrobial agent was administered either subcutaneously or orally one hour after infection. Surviving mice were observed daily for 10 days.

REFERENTIAL EXAMPLE 3

The minimum inhibitory concentrations (MIC) of known antimicrobial agents against various organisms were examined using Mueller-Hinton liquid medium (Difco) inoculated with $10^n$ microorganism and incubated at 37° C. for 24 hours. The results are shown in Table 1.

TABLE 1

(unit: μg/ml)

| | Drug | | | | | | | | | |
|---|---|---|---|---|---|---|---|---|---|---|
| | Cephalosporin | | | | | | | | Penicillin | |
| Organism | CEZ | CEX | CTX | CAZ | CPZ | CTT* | LMOX | CFS | IPC | AB-PC |
| Pseudomonas aeruginosa GNB-139 | >200 | >200 | 6.26 | 0.78 | 3.13 | >200 | 6.25 | 6.2 | 3.13 | 6.0 |
| Escherichia coli C-11 | 1.56 | 1.56 | <0.05 | <0.05 | 0.1 | <0.05 | <0.05 | 12.5 | <0.05 | 1.56 |
| Klebsiella pneumoniae 3K-25 | 1.56 | 1.56 | 0.1 | 0.2 | 0.39 | 0.2 | 0.2 | 50 | 1.56 | 25 |
| Serratia marcescens TO-101 | >200 | >200 | 0.78 | 0.1 | 3.13 | 1.56 | 0.39 | 100 | 6.25 | 100 |
| Staphylococcus aureus JU-5 | 0.78 | 12.5 | 3.13 | 12.5 | 3.13 | — | 12.5 | 3.13 | 12.5 | 3.13 |
| Streptococcus pyogenes Sv | 0.2 | 1.56 | 0.2 | 0.2 | 0.1 | — | 0.78 | — | 0.70 | 3.13 |
| Candida albicans U50-1 | — | — | — | — | — | — | — | — | — | — |

(unit: μg/ml)

| | Drug | | | | | |
|---|---|---|---|---|---|---|
| | Aminoglycoside | | | Pyridone carboxylic acid | | Others |
| Organism | GM | AMK | DBK | NA** | OFLX | Amp-B |
| Pseudomonas aeruginosa GNB-139 | 0.78 | 1.56 | 1.56 | 100 | 1.56 | — |
| Escherichia coli C-11 | 0.2 | 0.4 | — | 6.26 | 0.05 | — |
| Klebsiella pneumoniae 3K-25 | 0.39 | 1.56 | — | 3.1 | 0.025 | — |
| Serratia marcescens TO-101 | 0.39 | 0.78 | — | 6.25 | 0.2 | — |
| Staphylococcus | 0.78 | 3.12 | — | 50 | 0.2 | — |

TABLE 1-continued

|  |  |  |  |  |  |  |
|---|---|---|---|---|---|---|
| aureus JU-5 |  |  |  |  |  |  |
| Streptococcus pyogenes Sv | — | — | — | — | — | — |
| Candida albicans U50-1 | — | — | — | — | — | 12.5 |

*CTT: Cefotetan
**NA: Nalidixic acid

REFERENTIAL EXAMPLE 4

The virulence of microorganisms was examined using normal and CPA-treated mice. Mice were infected with serial 10-fold dilutions of microorganisms 4 days after CPA or saline. As shown in Table 2, when the virulence was expressed by the 50% lethal dose (LD$_{50}$), the susceptibility of CPA-treated mice against all bacterial and yeast strains tested was actually enhanced.

REFERENTIAL EXAMPLE 5

Normal mice were infected with various microorganisms and one hour later, selected antimicrobial agents were administered to them. The therapeutic effect (ED$_{50}$) of each agent is shown in Table 3.

TABLE 2

| Organism | Route of infection | CPA treatment | Dose$^{(a)}$ | | | | | | | | LD$_{50}$ (cfu/mouse) |
|---|---|---|---|---|---|---|---|---|---|---|---|
|  |  |  | $10^1$ | $10^2$ | $10^3$ | $10^4$ | $10^5$ | $10^6$ | $10^7$ | $10^8$ |  |
| Pseudomonas aeruginosa GNB-139 | ip | physiological saline |  |  |  | 5/5$^{(b)}$ | 4/5 | 1/5 |  |  | 6.8 · 10$^5$ |
|  |  | 200 mg/kg | 5/5 | 3/5 | 2/5 | 0/5 |  |  |  |  | 7.1 · 10$^2$ |
|  | sc | physiological saline |  |  |  |  | 5/5 | 4/5 | 3/5 | 2/5 | 3.9 · 10$^7$ |
|  |  | 200 mg/kg | 4/4 | 0/4 | 1/4 | 0/4 |  |  |  |  | 1.3 · 10$^2$ |
| Escherichia coli C-11 | ip | physiological saline |  |  |  |  | 4/4 | 4/4 | 4/4 | 2/4 | 1.1 · 10$^8$ |
|  |  | 200 mg/kg |  |  |  |  | 4/4 | 4/4 | 3/3 | 0/3 | 3.6 · 10$^7$ |
| Klebsiella pneumoniae 3K-25 | ip | physiological saline |  |  |  |  | 5/5 | 5/5 | 0/5 | 0/5 | 1.2 · 10$^7$ |
|  |  | 200 mg/kg |  |  |  |  | 5/5 | 4/5 | 0/5 | 0/5 | 7.6 · 10$^6$ |
| Serratia marcescens TO-101 | ip | physiological saline |  |  |  |  | 3/3 | 3/3 | 1/3 | 0/3 | 1.1 · 10$^7$ |
|  |  | 200 mg/kg |  |  |  |  | 5/5 | 0/5 | 0/5 | 0/5 | 5.5 · 10$^5$ |
| Staphylococcus aureus JU-5 | iv | physiological saline |  |  |  |  | 3/3 | 3/3 | 3/4 |  | 8.0 · 10$^7$ |
|  |  | 200 mg/kg |  |  |  | 3/3 | 2/3 | 0/4 | 0/4 |  | 7.2 · 10$^5$ |
| Streptococcus pyogenes Sv | ip | physiological saline | 3/5 | 0/5 | 0/5 |  |  |  |  |  | 25 |
|  |  | 200 mg/kg | 0/5 | 0/5 | 0/5 |  |  |  |  |  | <10 |
| Candida albicans U50-1 | iv | physiological saline |  |  |  |  | 5/5 | 5/5 | 0/5 | 0/5 | 1.8 · 10$^6$ |
|  |  | 200 mg/kg |  |  |  |  | 5/5 | 0/5 | 0/5 | 0/5 | 1.8 · 10$^5$ |

$^{(a)}$Injection into 7-9 week old male ICR mice.
$^{(b)}$Dead mice could be counted 7 days after infection.

TABLE 3

(unit: mg/kg)

| Organism | Drug | | | | | | | | | |
|---|---|---|---|---|---|---|---|---|---|---|
|  | Cephalosporin | | | | Penicillin | | Aminoglycoside | | | Others |
|  | CEZ | CEX | CPZ | CFS | PIPC | AB-PC | GM | AMK | DBK | Amp-B |
| Pseudomonas aeruginosa GNB-139 (1.6 × 10$^7$, ip) | >800 | >800 | >800 | 418 | >800 | >800 | 19.5 | 22 | 20 | — |
| Escherichia coli C-11 (5 × 10$^8$, ip) | 52.2 | — | 105 | 663 | 148 | 45 | — | 8.5 | — | — |
| Klebsiella pneumoniae 3K-25 (7.3 × 10$^6$, ip) | 240 | >800 | 35.2 | >800 | 45 | 400 | 10.3 | 20 | — | — |
| Serratia marcescens TO-101 (2.0 × 10$^7$, ip) | >800 | >800 | 120 | >800 | 100 | >800 | 8.8 | 19 | 6.5 | — |
| Staphylococcus aureus JU-5 (1.8 × 10$^7$, ip) | 2.0 | 25 | 1.3 | — | 2.5 | 4.0 | — | — | — | — |
| Streptococcus pyogenes Sv (2.1 × 10$^6$, iv) | 0.75 | 10 | — | >800 | 2.9 | 1.1 | — | — | — | — |
| Candida albicans U50-1 (2 × 10$^6$, iv) | — | — | — | — | — | — | — | — | — | 6.0 |

EXAMPLE

On the basis of the results obtained in Referential Examples 3-5, CPA-treated mice were treated with G-CSF, infected with microorganisms, and treated one hour later with antimicrobial agents. The results are shown in Table 4.

All control mice were killed by an infection with $1.3 \times 10^6$ *Pseudomonas aeruginosa* GNB-139. Group of 10 mice, administered either 200 mg/kg of Sefsulodin (CFS), 100 mg/kg of Ceftazidine (CAZ) or 200 mg/kg of Piperacillin (PIPC) were also killed. In the groups that were given 1 μg of G-CSF four times on a once-a-day basis prior to treatment with antimicrobial agents, either all or seven out of ten animals survived. In the group of mice that were infected with $13 \times 10^6$ *Pseudomonas aeruginosa* GNB-139 and which were subjected to pretreatment with G-CSF and post-treatment with 10 mg/kg of Dibekacin (DBK) plus 200 mg/kg of Cefsulodin (CFS), all animals survived. In the remaining group of mice that were infected with $130 \times 10^6$ *Pseudomonas aeruginosa* GNB-139 and which were subjected to pretreatment with G-CSF and post-treatment with 50 mg/kg of Gentamicin (GM), seven out of ten animals survived. These results clearly show that G-CSF enhanced the ability of the antimicrobial agents to cure infection.

Table 4 also shows that infection with *E. coli* C-11 was treated more effectively by pretreatment with G-CSF than when Cefazolin (CEZ), Cefoperazone (CPZ), Ampicillin (AB-PC) or Cephalexin (CEX) was administered alone.

The effectiveness of pretreatment with G-CSF was also apparent in infection with *Klebsiella pneumoniae* 3K-25, and it enhanced the therapeutic effect of each of Sefotax (CTX), Latamoxef (LMOX) and Piperacillin (PIPC).

In infection with *Serratia marcescens* TO-101, pretreatment with G-CSF also enhanced the therapeutic effect of each of Latamoxef (LMOX), Gentamicin (GM) and Ofloxacin (OFLX).

Also, in intravenous infection with *Streptococcus pyogenes* Sv, pretreatment with G-CSF enhanced the therapeutic effect of each of Cefazolin (CEZ), Cephalexin (CEX), Piperacillin (PIPC) and Ampicillin (AB-PC).

In intravenous infection with *Candida albicans* U50-1, pretreatment with G-CSF also enhanced the activity of an antifungal agent Amphotericin B (Amp-B)

As demonstrated in this example, it was possible for infection with the organisms listed above to be successfully treated by preliminary administration of G-CSF.

Equally good results can be attained by administering both G-CSF and antimicrobial agents after infection with the organisms.

TABLE 4

| Organism | Dose of infection | Route of infection | Survival rate (No. of live animals/No. of animals tested) | | |
|---|---|---|---|---|---|
| | | | Physiological saline | Antimicrobial agent only | Antimicrobial agent — G-CSF |
| *Pseudomonas aeruginosa* GNB-139 | 1,200 LD$_{50}$ (1.3 × 10$^6$ cells) | ip | 0/10 | CFS 200 mg/kg · sc 0/10 | 7/10 |
| | | | | CAZ 100 mg/kg · sc 0/10 | 10/10 |
| | | | | PIPC 200 mg/kg · sc 0/10 | 10/10 |
| | 12,000 LD$_{50}$ (13 × 10$^6$ cells) | ip | 0/10 | DBK 10 mg/kg · sc — CFS 200 mg/kg · sc 0/10 | 10/10 |
| | 120,000 LD$_{50}$ (130 × 10$^6$ cells) | ip | 0/10 | GM 50 mg/kg · sc 0/10 | 7/10 |
| *Escherichia coli* C-11 | 10 LD$_{50}$ (360 × 10$^7$ cells) | ip | 0/10 | CEZ 100 mg/kg · sc 0/10 | 10/10 |
| | | | | CPZ 200 mg/kg · sc 0/10 | 9/10 |
| | | | | AB-PC 150 mg/kg · sc 0/10 | 10/10 |
| | | | | CEX 200 mg/kg · po 0/10 | 4/10 |
| *Klebsiella pneumoniae* 3K-25 | 5 LD$_{50}$ (4.0 × 10$^7$ cells) | ip | 0/10 | CTX 50 mg/kg · sc 3/10 | 8/10 |
| | | | | LMOX 50 mg/kg · sc 2/10 | 6/10 |
| | | | | PIPC 100 mg/kg · sc 0/10 | 9/10 |
| *Serratia marcescens* TO-101 | 10 LD$_{50}$ (5.5 × 10$^6$ cells) | ip | 0/10 | LMOX 50 mg/kg · sc 4/10 | 10/10 |
| | | | | GM 20 mg/kg · sc 2/10 | 8/10 |
| | | | | OFLX 50 mg/kg · sc 4/10 | 10/10 |
| *Staphylococcus aureus* JU-5 | 27 LD$_{50}$ (1.8 × 10$^8$ cells) | ip | 0/10 | CEZ 2.0 mg/kg · sc 2/10 | 10/10 |
| | | | | AB-PC 2.0 mg/kg · sc 0/10 | 6/10 |
| *Streptococcus pyogenes* Sv | 10 LD$_{50}$ (7.2 × 10$^6$ cells) | iv | 0/10 | CEZ 20 mg/kg · sc 3/10 | 9/10 |
| | | | | CEX 20 mg/kg · po 0/10 | 4/10 |
| | | | | PIPC 10 mg/kg · sc 0/10 | 7/10 |
| | | | | AB-PC 10 mg/kg · sc 2/10 | 10/10 |
| *Candida* | 3 LD$_{50}$ | iv | 0/10 | Amp-B 10 mg/kg · iv | |

TABLE 4-continued

| Organism | Dose of infection | Route of infection | Survival rate (No. of live animals/No. of animals tested) | | |
|---|---|---|---|---|---|
| | | | Physiological saline | Antimicrobial agent only | Antimicrobial agent + G-CSF |
| albicans U50-1 | (0.6 × 10⁶ cells) | | | 1/10 | 6/10 |

As described in detail on the foregoing pages, chemotherapy of infectious diseases with entimicrobial agents can be accomplished very effectively by administering G-CSF either before or after the occurrence of infection. This method of the present invention is so efficacious that it is capable of curing the infectious diseases that have so far been considered refractory. According to the present invention, the use of antimicrobial agents can be reduced to such an extent that the side effects which have been considered to be serious problems in chemotherapy can be dramatically suppressed.

What is claimed is:

1. A method of treating an infectious disease comprising administering both isolated human granulocyte colony stimulating factor and an antimicrobial agent.

2. A method according to claim 1 wherein said granulocyte colony stimulating factor and antimicrobial agent are administered to a patient who is or will be immunocompromised.

3. A method according to claim 1 wherein said granulocyte colony stimulating factor and antimicrobial agent are administered to a patient who has been or will be exposed to microbial infection.

4. A method according to claim 1 wherein said granulocyte colony stimulating factor has the following physiochemical properties:

i) molecular weight: about 19,000 ±1,000 as measured by electrophoresis through a sodium dodecylsulfate-polyacrylamide gel;
 ii) isoelectric point: having at least one of the three isoelectric points, pI=5.5±0.1, pI=5.8±0.1, and pI=6.1±0.1;
 iii) ultraviolet absorption: having a maximum absorption at 280 nm and a minimum absorption at 250 nm;
 iv) amino acid sequence of the 21 residue from N terminus:

$H_2N$—Thr—Pro—Leu—Gly—Pro—Ala—Ser—Ser—Leu—Pro—Gln—Ser—Phe—Leu—Leu—Lys—Cys—Leu—Glu—Gln—Val—.

5. A method according to claim 1 wherein 0.1-500 μg of said granulocyte colony stimulating factor is administered at least once per week.

6. A method according to claim 5 wherein 0.5-200 μg of said granulocyte colony stimulating factor is administered.

7. A method according to claim 1 wherein said granulocyte colony stimulating factor comprises either a polypeptide having human granulocyte colony stimulating factor activity which is represented by the amino acid sequence shown below, or a glycoprotein having both said polypeptide and a sugar chain portion:

(Met)$_n$—Thr—Pro—Leu—Gly—Pro—Ala—Ser—Ser—Leu—
Pro—Gln—Ser—Phe—Leu—Leu—Lys—Cys—Leu—Glu—
Gln—Val—Arg—Lys—Ile—Gln—Gly—Asp—Gly—Ala—
Ala—Leu—Gln—Glu—Lys—Leu—(Val—Ser—Glu)$_m$—Cys—
Ala—Thr—Tyr—Lys—Leu—Cys—His—Pro—Glu—Glu—
Leu—Val—Leu—Leu—Gly—His—Ser—Leu—Gly—Ile—
Pro—Trp—Ala—Pro—Leu—Ser—Ser—Cys—Pro—Ser—
Gln—Ala—Leu—Gln—Leu—Ala—Gly—Cys—Leu—Ser—
Gln—Leu—His—Ser—Gly—Leu—Phe—Leu—Tyr—Gln—
Gly—Leu—Leu—Gln—Ala—Leu—Glu—Gly—Ile—Ser—
Pro—Glu—Leu—Gly—Pro—Thr—Leu—Asp—Thr—Leu—
Gln—Leu—Asp—Val—Ala—Asp—Phe—Ala—Thr—Thr—
Ile—Trp—Gln—Gln—Met—Glu—Glu—Leu—Gly—Met—
Ala—Pro—Ala—Leu—Gln—Pro—Thr—Gln—Gly—Ala—
Met—Pro—Ala—Phe—Ala—Ser—Ala—Phe—Gln—Arg—
Arg—Ala—Gly—Gly—Val—Leu—Val—Ala—Ser—His—
Leu—Gln—Ser—Phe—Leu—Glu—Val—Ser—Tyr—Arg—
Val—Leu—Arg—His—Leu—Ala—Gln—Pro (provided that m is 0 or 1 and n is 0 or 1).

8. A method according to claim 1 wherein the granulocyte colony stimulating factor is administered after exposure to microbial infection.

* * * * *